(12) United States Patent
Onik et al.

(10) Patent No.: US 10,154,869 B2
(45) Date of Patent: Dec. 18, 2018

(54) SYSTEM AND METHOD FOR CREATING RADIO-FREQUENCY ENERGY ELECTRICAL MEMBRANE BREAKDOWN FOR TISSUE ABLATION

(71) Applicants: Gary M. Onik, Ft. Lauderdale, FL (US); James A. Miessau, Branford, CT (US)

(72) Inventors: Gary M. Onik, Ft. Lauderdale, FL (US); James A. Miessau, Branford, CT (US)

( * ) Notice: Subject to any disclaimer, the term of this patent is extended or adjusted under 35 U.S.C. 154(b) by 769 days.

(21) Appl. No.: 14/451,333

(22) Filed: Aug. 4, 2014

(65) Prior Publication Data

US 2015/0150618 A1 Jun. 4, 2015

Related U.S. Application Data

(60) Provisional application No. 61/861,565, filed on Aug. 2, 2013, provisional application No. 61/867,048, filed on Aug. 17, 2013.

(51) Int. Cl.
*A61B 18/18* (2006.01)
*A61B 18/00* (2006.01)
(Continued)

(52) U.S. Cl.
CPC .............. *A61B 18/00* (2013.01); *A61B 18/12* (2013.01); *A61B 2018/00577* (2013.01);
(Continued)

(58) Field of Classification Search
CPC . A61L 2018/00577; A61L 2018/00821; A61L 18/00; A61L 18/12; A61L 18/14;
(Continued)

(56) References Cited

U.S. PATENT DOCUMENTS 6,214,297 B1  4/2001  Zhang et al.
7,113,821 B1  9/2006  Sun et al.
(Continued)

OTHER PUBLICATIONS

Antoni Ribas et al., Dendritic Cell Vaccination Combined with CTLA4 Blockade in Patients with Metastic Melanoma, Oct. 1, 2009, 15, 19, 6267-6275.*
(Continued)

*Primary Examiner* — Michael Peffley
*Assistant Examiner* — Amanda Zink
(74) *Attorney, Agent, or Firm* — Baker Donelson; Emily R. Billig

(57) ABSTRACT

A method of non-thermally ablating undesirable tissue in the body by application of pulsed, bi-polar, instant charge reversal electrical fields of sufficient energy to cause complete and immediate cell membrane rupture and destruction. Energy is delivered through radio frequency pulses of particular frequencies, wave characteristics, pulse widths and pulse numbers, such that enhanced physical stresses are placed on the cell membrane to cause its immediate and complete destruction thereby spilling the entire cell content and membrane constituents into the extracellular space without denaturing proteins so as to enable an immunological response to destroy and remove the target tissue and similarly marked tissue elsewhere in the subject.

28 Claims, 9 Drawing Sheets

(51) Int. Cl.
*A61B 18/12* (2006.01)
*A61B 18/14* (2006.01)

(52) U.S. Cl.
CPC .............. *A61B 2018/00761* (2013.01); *A61B 2018/00821* (2013.01); *A61B 2018/00988* (2013.01); *A61B 2018/143* (2013.01)

(58) Field of Classification Search
CPC ....... A61L 18/1477; A61L 2017/00061; A61L 2017/00159; A61L 2018/00732; A61L 2018/00761; A61L 2018/00875; A61L 2018/00988; A61L 2018/126; A61L 2018/143; A61L 5/14532
See application file for complete search history.

(56) References Cited

U.S. PATENT DOCUMENTS

| | | | |
|---|---|---|---|
| 7,680,543 B2* | 3/2010 | Azure | A61B 18/1477 606/41 |
| 7,853,333 B2 | 12/2010 | Demarais | |
| 7,937,143 B2 | 5/2011 | Demarais et al. | |
| 7,938,824 B2 | 5/2011 | Chornenky | |
| 8,048,067 B2 | 11/2011 | Davalos et al. | |
| 8,114,070 B2 | 2/2012 | Rubinsky et al. | |
| 8,131,371 B2 | 3/2012 | Demarais et al. | |
| 8,221,411 B2 | 7/2012 | Francischelli et al. | |
| 8,226,648 B2 | 7/2012 | Paul et al. | |
| 8,231,603 B2 | 7/2012 | Hobbs et al. | |
| 8,282,631 B2 | 10/2012 | Davalos et al. | |
| 8,465,484 B2 | 6/2013 | Davalos et al. | |
| 2005/0288730 A1 | 12/2005 | Deem et al. | |
| 2006/0041277 A1 | 2/2006 | Deem et al. | |
| 2007/0043345 A1 | 2/2007 | Davalos et al. | |
| 2007/0066957 A1 | 3/2007 | Demarais et al. | |
| 2007/0083239 A1 | 4/2007 | Demarais et al. | |
| 2007/0129720 A1 | 6/2007 | Demarais et al. | |
| 2008/0132884 A1* | 6/2008 | Rubinsky | A61B 18/1477 606/34 |
| 2009/0326366 A1 | 12/2009 | Krieg | |
| 2010/0023004 A1 | 1/2010 | Francischelli et al. | |
| 2010/0030211 A1 | 2/2010 | Davalos et al. | |
| 2010/0152725 A1 | 6/2010 | Pearson et al. | |
| 2010/0179530 A1 | 7/2010 | Long et al. | |
| 2010/0249771 A1 | 9/2010 | Pearson et al. | |
| 2010/0250209 A1 | 9/2010 | Pearson et al. | |
| 2010/0261994 A1 | 10/2010 | Davalos et al. | |
| 2010/0262067 A1 | 10/2010 | Chornenky et al. | |
| 2011/0106221 A1* | 5/2011 | Neal, II | C12N 13/00 607/74 |
| 2011/0112520 A1 | 5/2011 | Michael | |
| 2011/0160514 A1 | 6/2011 | Long et al. | |
| 2011/0166499 A1 | 7/2011 | Demarais et al. | |
| 2011/0190659 A1 | 8/2011 | Long et al. | |
| 2011/0190764 A1 | 8/2011 | Long et al. | |
| 2012/0021481 A1 | 1/2012 | Hebner et al. | |
| 2012/0071872 A1 | 3/2012 | Rubinsky et al. | |
| 2012/0071874 A1 | 3/2012 | Davalos et al. | |
| 2012/0109122 A1 | 5/2012 | Arena et al. | |
| 2012/0143181 A1 | 6/2012 | Demarais et al. | |
| 2012/0190040 A1 | 7/2012 | Talebpour et al. | |
| 2012/0215218 A1 | 8/2012 | Lipani | |
| 2012/0220998 A1* | 8/2012 | Long | A61B 18/1206 606/41 |
| 2012/0220999 A1 | 8/2012 | Long | |
| 2012/0221002 A1 | 8/2012 | Long et al. | |
| 2012/0252087 A1 | 10/2012 | Hebner et al. | |
| 2012/0253188 A1 | 10/2012 | Holland | |
| 2012/0277741 A1 | 11/2012 | Davalos et al. | |

OTHER PUBLICATIONS

Arena, C.B. et al. "High-Frequency Irreversible Electroporation (H-FIRE) for Non-Thermal Ablation without Muscle Contraction", Biomed Eng. Online (Nov. 21, 2011).
U.S. Food and Drug Administration, "Kinetics of Microbial Inactivation for Alternative Food Processing Technologies—Pulsed Electric Fields", A Report of the Institute of Food Technologists for the Food and Drug Administration of the U. S. Department of Health and Human Services (Mar. 29, 2000).
Li, X. et al. "Immunologic Response to Tumor Ablation with Irreversible Electroporation", PLoS One (Nov. 6, 2012).
Hillen et al. "Treatment of Metastatic Posterior Vertebral Body Osseous Tumors by Using a Targeted Bipolar Radiofrequency Ablation Device: Technical Note", Radiology (Jun. 13, 2014).
Chang, D.C. et al. "Changes in Membrane Structure Induced by Electroporation as Revealed by Rapid-Freezing Electron Microscopy", 58 Biophys J 01 (Jul. 1990).
Neal et al. "In Vitro and Numerical Support for Combinatorial Irreversible Electroporation and Electrochemotherapy Glioma Treatment", Annals of Biomedical Engineering, 42(3): 475-487 (Mar. 2014).
Waitz R. et al. "Potent Induction of Tumor Immunity by Combining Tumor Cryoablation with Anti-CTLA-4 Therapy", Cancer Res 2012, 72:430-439 (Nov. 22, 2011).
Kawano, M. et al. "Cryoimmunologic Antitumor Effects Enhanced by Dendritic Cells in Osteosarcoma", Clin Orthop Relat Res. May 2010; 468(5): 1373-1383.
Sabel, M.S. et al. "Immunologic Response to Cryoablation of Breast Cancer", Breast Cancer Research and Treatment 2005 90: 97-104.
Onik, G. et al. "Irreversible Electroporation: Implications for Prostate Ablation", Technology in Cancer Res. and Treatment, Aug. 2007; 6(4): 295-300.
Ma, Chun-Hua et al. Experimental Study on Residual Tumor Angiogenesis after Cryoablation Asian Pac J Cancer Prev, 2014, 15 (6), 2491-2494.

* cited by examiner

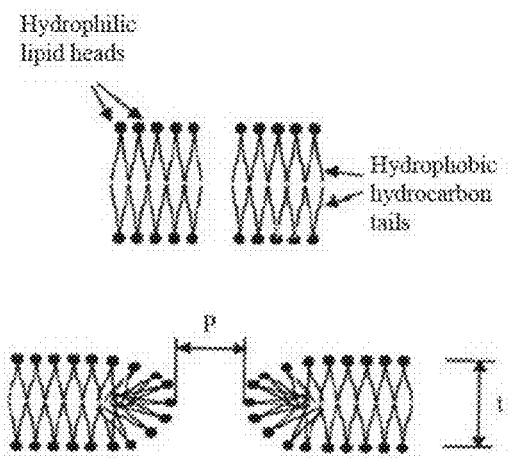
Fig. 1 - Prior Art
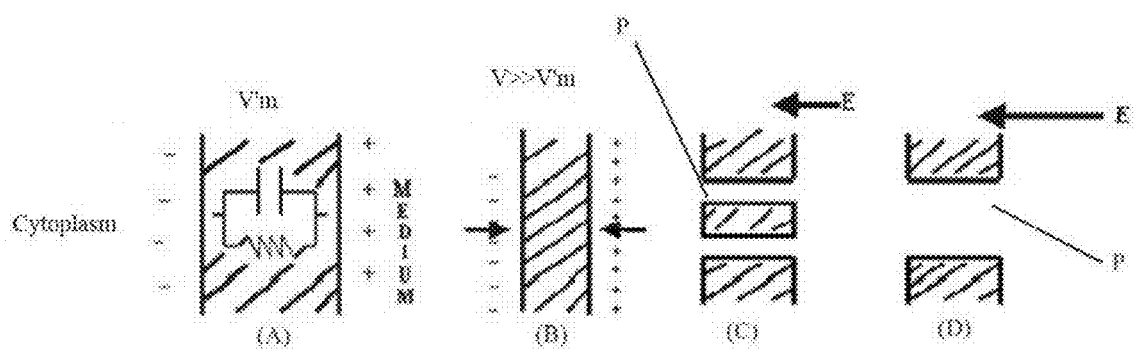
Fig. 2 - Prior Art

Probe distance = 1cm

| Protocol | Pulse Width | Pulse Number | Volts/cm | Energy (mJ) | Total Time | |
|---|---|---|---|---|---|---|
| 1* | 10 ms | 83 | 600 kV | 10.38 | .83 s | |
| 2 | 200 us | 2490 | 10 kV | 10.38 | .49 s | |
| 3 | 200 us | 2490+ | 10 kV or less | 10.38 | .49 s + | Additional pulses added for decreased voltage caused by feedback |
| 4 | 200 us | 2490+ | 10 kV | 10.38 + | 4.9 s + | Additional pulses added for less efficient higher frequency |

SYSTEM AND METHOD FOR CREATING RADIO-FREQUENCY ENERGY ELECTRICAL MEMBRANE BREAKDOWN FOR TISSUE ABLATION

CROSS REFERENCE TO RELATED APPLICATIONS

This patent application claims priority to U.S. Provisional Patent Application No. 61/861,565 filed on Aug. 2, 2013 and titled "Device and Process For Creating Radio-Frequency Energy Electrical Membrane Breakdown (RF-EMB) For Tissue Ablation," which is here incorporated in its entirety by reference. This patent application also claims priority to U.S. Provisional Patent Application No. 61/867,048 filed on Aug. 17, 2013 and titled "Radio-Frequency Energy Electrical Membrane Breakdown Using An Instant Charge Reversal Pulse Generator," which is here incorporated in its entirety by reference.

BACKGROUND OF THE INVENTION

1. Field of the Invention

The present invention relates generally to the field of medical ablation of biological tissue for treatment of disease and, more particularly, to the controlled application of radio frequency energy to soft tissue and cancerous tissue in humans and mammals to ablate such tissue through cellular destruction by Electrical Membrane Breakdown.

2. Description of the Background

Cancer is not one single disease but rather a group of diseases with common characteristics that often result in sustained cell proliferation, reduced or delayed cell mortality, cooption of bodily angiogenesis and metabolic processes and evasion of bodily immune response which results in undesirable soft tissue growths called neoplasms or, more commonly, tumors. Removal or destruction of this aberrant tissue is a goal of many cancer treatment methods and modalities. Surgical tumor excision is one method of accomplishing this goal. Tissue ablation is another, minimally invasive method of destroying undesirable tissue in the body, and has been generally divided into thermal and non-thermal ablation technologies. Thermal ablation encompasses both the addition and removal of heat to destroy undesirable cells. Cryoablation is a well established technique that kills cells by freezing of the extracellular compartment resulting in cell dehydration beginning at −15 C and by intracellular ice formation causing membrane rupture occurring at colder temperatures. Because cryoablative techniques can rupture the cell membrane without denaturing cell proteins under certain conditions, such techniques have the additional ability to stimulate an antitumor immune response in the patient.

Heat based techniques are also well established for ablation of both cancerous and non cancerous tissues and include radio-frequency (RF) thermal, microwave and high intensity focused ultrasound ablation which raise localized tissue temperatures well above the body's normal 37° C. These methods use various techniques to apply energy to the target cells to raise interstitial temperature. For example, RF thermal ablation uses a high frequency electric field to induce vibrations in the cell membrane that are converted to heat by friction. Cell death occurs in as little as 30 second once the cell temperature reaches 50° C. and decreases as the temperature rises. At 60° C. cell death is instantaneous. If the intracellular temperature rises to between about 60 and 95° C., the mechanisms involved in cell death include cellular desiccation and protein coagulation. When the intracellular temperature reaches 100° C., cellular vaporization occurs as intracellular water boils to steam. In the context of tissue ablation, cell temperatures not exceeding 50° C. are not considered clinically significant. Because cellular proteins are denatured by the heat of thermal ablation techniques, they are not available to stimulate a specific immune response as they may be with cryoablation. Both heat based and cryoablation techniques suffer from the drawback that they have little or no ability to spare normal structures in the treatment zone and so can be contraindicated based on tumor location or lead to complications from collateral injury.

Non thermal ablation techniques include electrochemotherapy and irreversible electroporation which although quite distinct from one another, each rely on the phenomenon of electroporation. With reference to FIG. 1, electroporation refers to the fact that the plasma membrane of a cell exposed to high voltage pulsed electric fields becomes temporarily permeable due to destabilization of the lipid bilayer and the formation of pores P. The cell plasma membrane consists of a lipid bilayer with a thickness t of approximately 5 nm. With reference to FIG. 2A, the membrane acts as a nonconducting, dielectric barrier forming, in essence, a capacitor. Physiological conditions produce a natural electric potential difference due to charge separation across the membrane between the inside and outside of the cell even in the absence of an applied electric field. This resting transmembrane potential V'm ranges from 40 mv for adipose cells to 85 mv for skeletal muscle cells and 90 mv cardiac muscle cells and can vary by cell size and ion concentration among other things.

With continued reference to FIGS. 2B-2D, exposure of a cell to an externally applied electric field E induces an additional voltage V across the membrane as long as the external field is present. The induced transmembrane voltage is proportional to the strength of the external electric field and the radius of the cell. Formation of transmembrane pores P in the membrane occurs if the cumulative resting and applied transmembrane potential exceeds the threshold voltage which may typically be between 200 mV and 1 V. Poration of the membrane is reversible if the transmembrane potential does not exceed the critical value such that the pore area is small in relation to the total membrane surface. In such reversible electroporation, the cell membrane recovers after the applied field is removed and the cell remains viable. Above a critical transmembrane potential and with long exposure times, poration becomes irreversible leading to eventual cell death due an influx of extracellular ions resulting in loss of homeostasis and subsequent apoptosis. Pathology after irreversible electroporation of a cell does not show structural or cellular changes until 24 hours after field exposure except in certain very limited tissue types. However, in all cases the mechanism of cellular destruction and death by IRE is apoptotic which requires considerable time to pass and is not visible pathologically in a time frame to be clinically useful in determining the efficacy of IRE treatment which is an important clinical drawback to the method.

Developed in the early 1990's, electrochemotherapy combines the physical effect of reversible cell membrane poration with administration of chemotherapy drugs such as cisplatin and bleomycin. By temporarily increasing the cell membrane permeability, uptake of non-permeant or poorly permeant chemotherapeutic drugs is greatly enhanced. After the electric field is discontinued, the pores close and the drug molecules are retained inside the target cells without significant damage to the exposed cells. This approach to chemotherapy grew out of earlier research developing electroporation as a technique for transfection of genes and DNA molecules for therapeutic effect. In this context, irreversible electroporation leading to cell death was viewed as a failure in as much as the treated cells did not survive to realize the modification as intended.

Irreversible electroporation (IRE) as an ablation method grew out of the realization that the "failure" to achieve reversible electroporation could be utilized to selectively kill undesired tissue. IRE effectively kills a predictable treatment area without the drawbacks of thermal ablation methods that destroy adjacent vascular and collagen structures. During a typical IRE treatment, one to three pairs of electrodes are placed in or around the tumor. Electrical pulses carefully chosen to induce an electrical field strength above the critical transmembrane potential are delivered in groups of 10, usually for nine cycles. Each 10-pulse cycle takes about one second, and the electrodes pause briefly before starting the next cycle. As described in U.S. Pat. No. 8,048,067 to Rubinsky, et. al and application Ser. No. 13/332,133 by Arena, et al. which are incorporated here by reference, the field strength and pulse characteristics are chosen to provide the necessary field strength for IRE but without inducing thermal effects as with RF thermal ablation. However, because cells ablated by IRE methods undergo apoptotic death without membrane rupture their ability to induce a supplemental immune response as observed with cryoablation is impaired. When used as the sole ablative tool in a treatment protocol, IRE's inability to induce a supplemental immune response is a substantial limitation to its therapeutic benefit for patients. On the other hand, cryoablation suffers from the significant clinical disadvantages arising from the extreme cold and its capacity to destroy nearby critical healthy structures. What is needed is a minimally invasive tissue ablation technology that can avoid damaging healthy tissue while exposing cellular contents without denaturing such cellular contents so that they can to trigger a clinically usefully immune response.

SUMMARY OF THE INVENTION

It is, therefore, an object of the present invention to provide a method of tissue ablation using electrical pulses which causes immediately cell death through the mechanism of breaking down the membrane of the cell.

It is another object of the present invention to provide a method of tissue ablation that causes immediate cell death electrically breaking down the cell membrane that can be monitored by immediate pathologic examination of the tissue to evaluate efficacy of the treatment.

It is yet another object of the present invention to provide a method of tissue ablation using electrical pulses that causes immediate cellular membrane breakdown non-thermally so that sensitive tissue structures are spared and cellular and membrane proteins are spilled into the extracellar space without denaturing to be exposed to the body's immune system in order to illicit a specific tumor immune response.

It is yet another object of the present invention to provide a method of tissue ablation that exposes non-denatured cellular and membrane proteins to the immune system to illicit a specific tumor immune response which can be modulated and enhanced by a variety of additional immune modulators.

According to the present invention, the above-described and other objects are accomplished, by applying to undesirable tissue in the body an external electric field specifically configured to directly and completely disintegrate the cell membrane. Referred to as Electrical Membrane Breakdown (EMB), application of an external oscillating electric field causes vibration and flexing of the cell membrane which results in a dramatic and immediate mechanical tearing or rupturing the cell membrane. EMB applies significantly higher energy levels than prior art methods to rupture the cell membrane rather than to electroporate the cell membrane. Unlike prior art methods, EMB expels the entire contents of the cell into the extracellular fluid and exposes internal components of the cell membrane which induces an immunologic response by the subject.

A system for generation of the electric field necessary to induce RF-EMB includes a bipolar pulse generator operatively coupled to a controller for controlling generation and delivery of the electrical pulses necessary to generate an appropriate electric field. The field is generated by therapeutic probes placed in proximity to the soft tissue or cancerous cells within the body of the subject and the bipolar pulses are shaped, designed and applied to achieve that result in an optimal fashion. A temperature probe may be provided for temperature feedback to the controller which is configured to control the signal output characteristics of the signal generator. The RF-EMB protocol calls for a series of short and intense bi-polar electric pulses to generate an oscillating electric field between the electrodes that induce a similarly rapid and oscillating buildup of transmembrane potential across the cell membrane. The built up charge applies a cyclic, oscillating force to the cellular membrane which upon reaching a critical value causes rupture of the membrane and spillage of the cellular content. In addition to being bi-polar, the electric pulses preferably trace a square wave form and are characterized by instant charge reversal that have substantially no relaxation time between the positive and negative polarities of the bi-polar pulse. Instant charge reversal pulses are significantly more effective in destruction of dielectric cell membranes Important characteristic of the applied electric field include the field strength (Volts/cm), frequency, polarity, shape, duration, number and spacing. Field strength (Volts/cm) is a function of both the applied voltage and the electrode spacing and is preferably in the range of 1,500 V/cm to 10,000 V/cm absent thermal considerations. RF-EMB ablation is preferably performed by application of a series of not less than 100 electric pulses in a pulse train so as to impart the energy necessary on the target tissue without developing thermal issues in any clinically significant way. The pulse duration is preferably from 100 to 1000 μs. The relationship between the duration and frequency of each pulse determines the number of instantaneous charge reversals experienced by the cell membrane during each pulse. The duration of each inter pulse burst interval is determined by the controller 14 based on thermal considerations. Real time temperature feedback of the treatment site may be provided to the controller which the controller can modulate treatment parameters to eliminate thermal effects as desired. Current flow at the treatment site may also be monitored for this purpose.

The EMB ablation method is carried out by first identifying the location of the soft tissue within the subject to be ablated by medical imaging techniques such as CT or MRI or other means. A preferred position and spacing of the electrodes relative to the target tissue is determined and from 1 to 6 needle electrodes connected to the controller and signal generator are inserted into position in and around the treatment site. Placement and positioning of the electrodes is confirmed by medical imaging and the pulse generator is activated to apply electrical pulses to the electrodes to generate the treatment field thereby causing electrical membrane breakdown of cells in the soft tissue.

Electrical membrane breakdown causes immediate spillage of all intracellular components of the ruptured cells into an extracellular space and exposes the internal constituent parts of the cell and cell membrane including antigens which induce an immunologic response to destroy and remove this and like material in the body of the subject. The immunologic response can be enhanced by administration of agents that increase the immunologic response process including drugs. Electrical membrane breakdown causes immediate, visually observable tissue change, cellular membrane destruction and cell death such that the method may include the biopsy of a portion of the treated target tissue to verify treatment efficacy immediately after completion of the treatment while the patient is still in position for additional treatment. In some situation, the mode of treatment may be switched from EMB to thermal ablation without removal or repositioning of the electrodes by reconfiguring the signal generated by the pulse generator to increase the tissue temperature at the electrodes according to known RF thermal techniques.

BRIEF DESCRIPTION OF THE DRAWINGS

FIG. 1 is a diagram of a cell membrane pore.

FIG. 2 is a diagram of cell membrane pore formation by a prior art method.

DETAILED DESCRIPTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not limit the scope of the invention.

Irreversible electroporation as a tissue ablation method is well developed with commercially manufactured equipment such as the NanoKnife by AngioDynamics (Latham, N.Y.) available on the market. As described, this ablation technique utilizes high electric field strengths to induce irreversible electroporation of the cell membrane resulting in cell death due to loss of homeostasis and apoptosis. The present invention also describes methods for ablating cells within the body of a subject utilizing high frequency and high strength electric fields but does so through the entirely different process of Electrical Membrane Breakdown (EMB). Electrical Membrane Breakdown is the application of an external oscillating electric field to cause vibration and flexing of the cell membrane which results in a dramatic and immediate mechanical tearing or rupturing the cell membrane. Unlike IRE in which pores are created but through which little or no content of the cell is released, EMB tears open the cell such that the entire contents of the cell are expelled into the extracellular fluid, and internal components of the cell membrane itself are exposed.

The present invention relies on the interaction of an applied electric field with the transmembrane potential but its similarity to IRE ends there. EMB applies significantly higher energy levels by specifically configured electric field profiles to directly and completely disintegrate the cell membrane rather than to electroporate the cell membrane. Others have demonstrated that the energy levels required for EMB is 100 times greater than for IRE using the same pulse configurations (pulse number and voltage density) delivered by currently available IRE equipment and protocols. The inability of current IRE methods and energy protocols to deliver the energy necessary to cause EMB explains why pathologic examination of IRE treated specimens has never shown the pathologic characteristics of EMB and is a critical reason why EMB had not until now been recognized as an alternative method of cell destruction.

Figure 9:
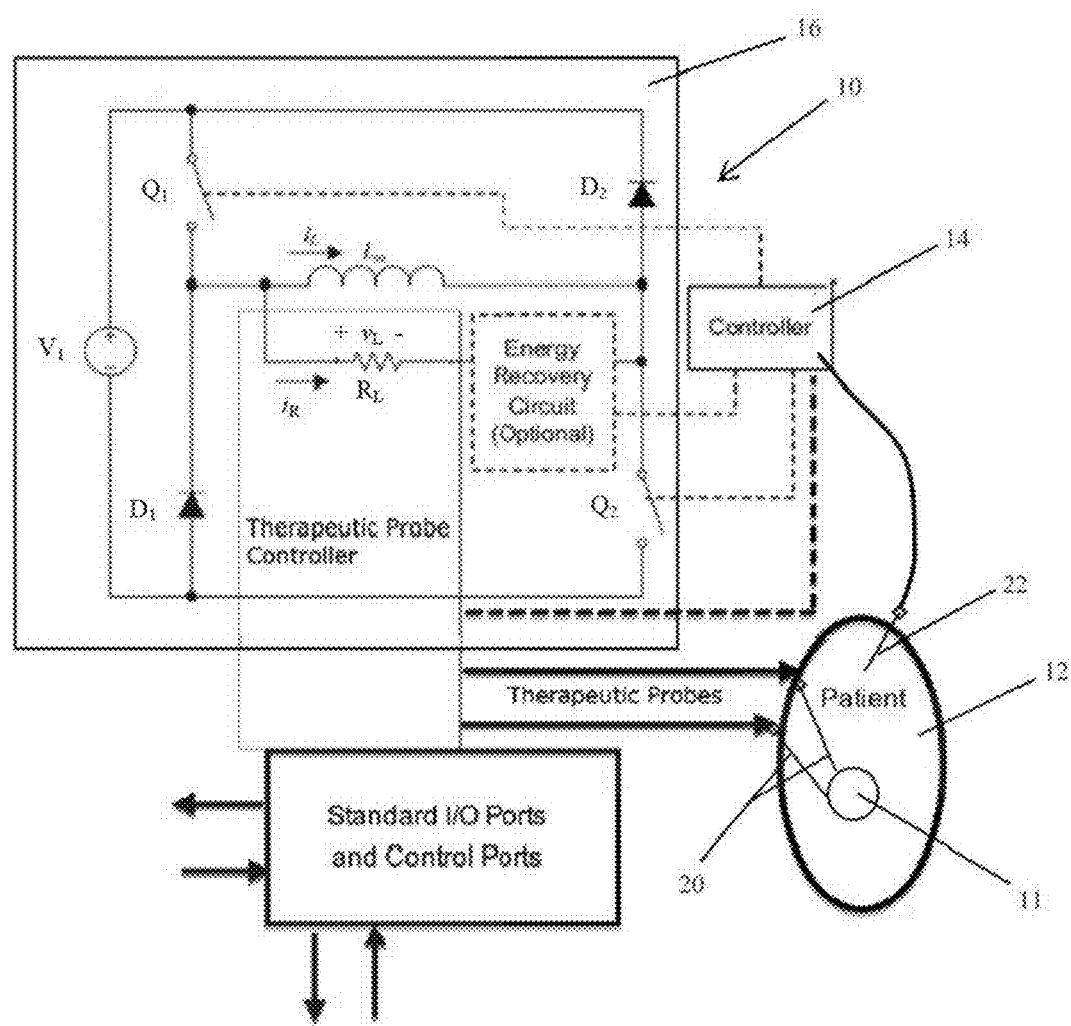
FIG. 9 is a schematic diagram of a pulse generation and delivery system for application of the method of the present invention.

FIG. 9 is a schematic diagram of a system 10 for generation of the electric field necessary to induce EMB of cells 11 within a patient 12. The system 10 includes a bipolar pulse generator 16 operatively coupled to a controller 14 for controlling generation and delivery to the therapeutic probe or probes 20 (two are shown) of the electrical pulses necessary to generate an appropriate electric field to achieve EMB. The therapeutic probes are placed in proximity to the soft tissue or cancerous cells 11 which are intended to be ablated through the process of EMB and the bipolar pulses are shaped, designed and applied to achieve that result in an optimal fashion. A temperature probe 22 may be provided for temperature measurement and feedback to the controller of the temperature at or near the electrodes. The controller may preferably include an onboard digital processor and a memory and may be a general purpose computer system, programmable logic controller or similar digital logic control device. The controller is preferably configured to control the signal output characteristics of the signal generation including the voltage, frequency, shape, polarity and duration of pulses as well as the total number of pulses delivered in a pulse train and the duration of the inter pulse burst interval.

With reference to FIG. 9, the EMB protocol calls for a series of short and intense bi-polar electric pulses delivered from the pulse generator through one or more therapeutic probes 20 (electrodes) inserted directly into, or placed around the target tissue 11. The bi-polar pulses generate an oscillating electric field between the electrodes that induce a similarly rapid and oscillating buildup of transmembrane potential across the cell membrane. The built up charge applies a force to the cellular membrane which upon reaching a critical value causes rupture of the membrane and spillage of the cellular content. Bipolar pulses are more lethal than monopolar pulses because the pulsed electric field causes movement of charged molecules in the cell membrane and reversal in the orientation or polarity of the electric field causes a corresponding change in the direction of movement of the charged molecules and of the forces acting on the cell. The added stresses that are placed on the cell membrane by alternating changes in the movement of charged molecules create additional internal and external changes that cause indentations, crevasses, rifts and irregular sudden tears in the cell membrane causing more extensive, diverse and random damage.

Figure 3:
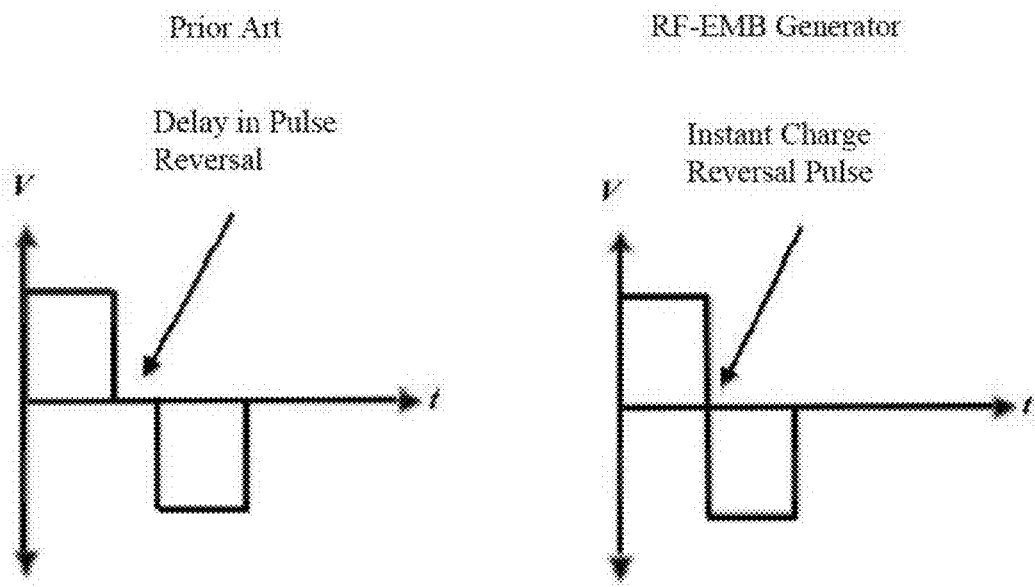
FIG. 3 is a comparison of a prior art charge reversal with an instant charge reversal according to the present invention.
Figure 4:
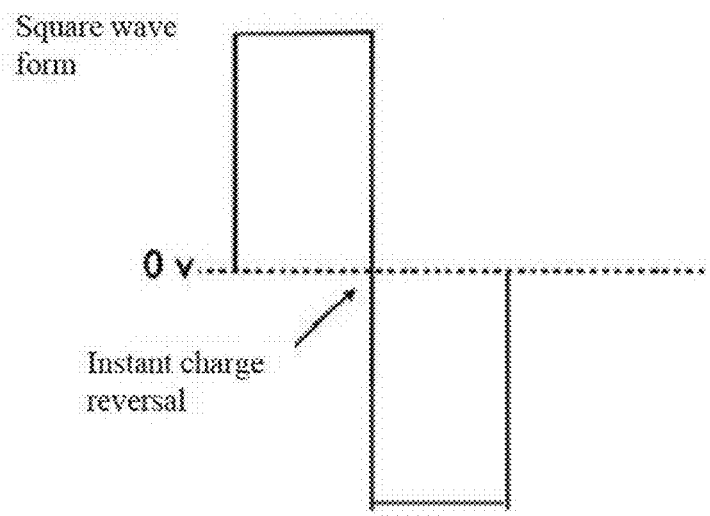
FIG. 4 is a square wave from instant charge reversal pulse according to the present invention.

With reference to FIG. 4, in addition to being bi-polar, the preferred embodiment of electric pulses is one for which the voltage over time traces a square wave form and is characterized by instant charge reversal pulses (ICR). A square voltage wave form is one that maintains a substantially constant voltage of not less than 80% of peak voltage for the duration of the single polarity portion of the trace, except during the polarity transition. An instant charge reversal pulse is a pulse that is specifically designed to ensure that substantially no relaxation time is permitted between the positive and negative polarities of the bi-polar pulse. That is, the polarity transition happens virtually instantaneously.

The destruction of dielectric cell membranes through the process of Electrical Membrane Breakdown is significantly more effective if the applied voltage pulse can transition from a positive to a negative polarity without delay in between. Instant charge reversal prevents rearrangement of induced surface charges resulting in a short state of tension and transient mechanical forces in the cells, the effects of which are amplified by large and abrupt force reversals. Alternating stress on the target cell that causes structural fatigue is thought to reduce the critical electric field strength required for EMB. The added structural fatigue inside and along the cell membrane results in or contributes to physical changes in the structure of the cell. These physical changes and defects appear in response to the force applied with the oscillating EMB protocol and approach dielectric membrane breakdown as the membrane position shifts in response to the oscillation, up to the point of total membrane rupture and catastrophic discharge. This can be analogized to fatigue or weakening of a material caused by progressive and localized structural damage that occurs when a material is subjected to cyclic loading, such as for example a metal paper clip that is subjected to repeated bending. The nominal maximum stress values that cause such damage may be much less than the strength of the material under ordinary conditions. The effectiveness of this waveform compared to other pulse waveforms can save up to $\frac{1}{5}$ or $\frac{1}{6}$ of the total energy requirement.

Figure 10:
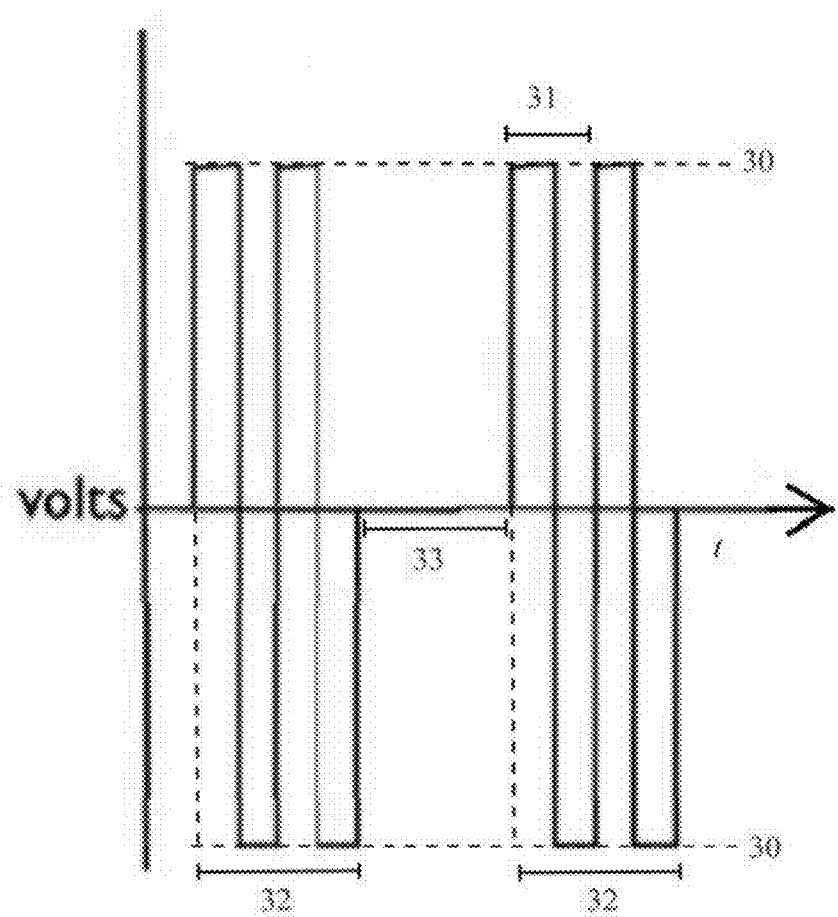
FIG. 10 is a diagram of the parameters of a partial pulse train according to the present invention.

With reference to FIG. 10, another important characteristic of the applied electric field is the field strength (Volts/cm) which is a function of both the voltage 30 applied to the electrodes by the pulse generator 16 and the electrode spacing. Typical electrode spacing for a bi-polar, needle type probe might be 1 cm, while spacing between multiple needle probe electrodes can be selected by the surgeon and might typically be from 0.75 cm to 1.5 cm. A pulse generator for application of the present invention is capable of delivering up to a 10 kV potential. The actual applied field strength will vary over the course of a treatment to control circuit amperage which is the controlling factor in heat generation, and patient safety (preventing large unanticipated current flows as the tissue impedance falls during a treatment). Where voltage and thus field strength is limited by heating concerns the duration of the treatment cycle may be extended to compensate for the diminished charge accumulation. Absent thermal considerations, a preferred field strength for EMB is in the range of 1,500 V/cm to 10,000 V/cm.

Figure 5:
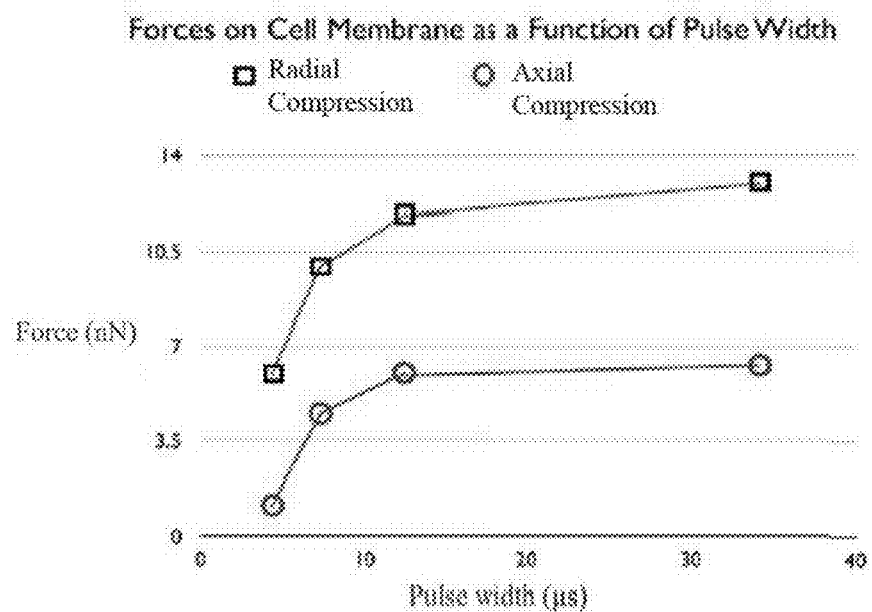
FIG. 5 is a diagram of the forces imposed on a cell membrane as a function of electric field pulse width according to the present invention.

With continued reference to FIG. 10, the frequency 31 of the electric signal supplied to the electrodes 20, and thus of the field polarity oscillations of the resulting electric field, influences the total energy imparted on the subject tissue and thus the efficacy of the treatment but are less critical than other characteristics. A preferred signal frequency is from 14.2 kHz to less than 500 kHz. The lower frequency bound imparts the maximum energy per cycle below which no further incremental energy deposition is achieved. With reference to FIG. 5, the upper frequency limit is set based on the observation that above 500 kHz, the polarity oscillations are too short to develop enough motive force on the cell membrane to induce the desired cell membrane distortion and movement. More specifically, at 500 kHz the duration of a single full cycle is 2 µs of which half is of positive polarity and half negative. When the duration of a single polarity approaches 1 µs there is insufficient time for charge to accumulate and motive force to develop on the membrane. Consequently, membrane movement is reduced or eliminated and EMB does not occur. In a more preferred embodiment the signal frequency is from 100 kHz to 450 kHz. Here the lower bound is determined by a desire to avoid the need for anesthesia or neuromuscular-blocking drugs to limit or avoid the muscle contraction stimulating effects of electrical signals applied to the body. The upper bound in this more preferred embodiment is suggested by the frequency of radiofrequency thermal ablation equipment already approved by the FDA, which has been deemed safe for therapeutic use in medical patients In addition to controlling the pulse amplitude 30, frequency 31, polarity and shape provided by the pulse generator 16, the logic controller 14 controls the number of pulses 32 to be applied in the treatment series or pulse train, the duration of each pulse 32, and the inter pulse burst delay 33. Although only two are depicted in FIG. 10 due to space constraints, RF-EMB ablation is preferably performed by application of a series of not less than 100 electric pulses 32 in a pulse train so as to impart the energy necessary on the target tissue 11 without developing thermal issues in any clinically significant way. The width of each individual pulse 32 is preferably from 100 to 1000 µs with an inter pulse burst interval 33 during which no voltage is applied in order to facilitate heat dissipation and avoid thermal effects. The relationship between the duration of each pulse 32 and the frequency 31 (period) determines the number of instantaneous charge reversals experienced by the cell membrane during each pulse 32. The duration of each inter pulse burst interval 33 is determined by the controller 14 based on thermal considerations. In an alternate embodiment the system 10 is further provided with a temperature probe 22 inserted proximal to the target tissue 11 to provide a localized temperature reading at the treatment site to the controller 14. The temperature probe 22 may be a separate, needle type probe having a thermocouple tip, or may be integrally formed with or deployed from one or more of the needle electrodes. With temperature feedback in real time, the controller can modulate treatment parameters to eliminate thermal effects as desired by comparing the observed temperature with various temperature set points stored in memory. More specifically, the controller can shorten or increase the duration of each pulse 32 to maintain a set temperature at the treatment site to, for example, create a heating (high temp) for the needle tract to prevent bleeding or to limit heating (low temp) to prevent any coagulative necrosis. The duration of the inter pulse burst interval can be modulated in the same manner in order to eliminate the need to stop treatment and maximizing the deposition of energy to accomplish RF-EMB. Pulse amplitude 30 and total number of pulses in the pulse train may also be modulated for the same purpose and result.

Figure 6:
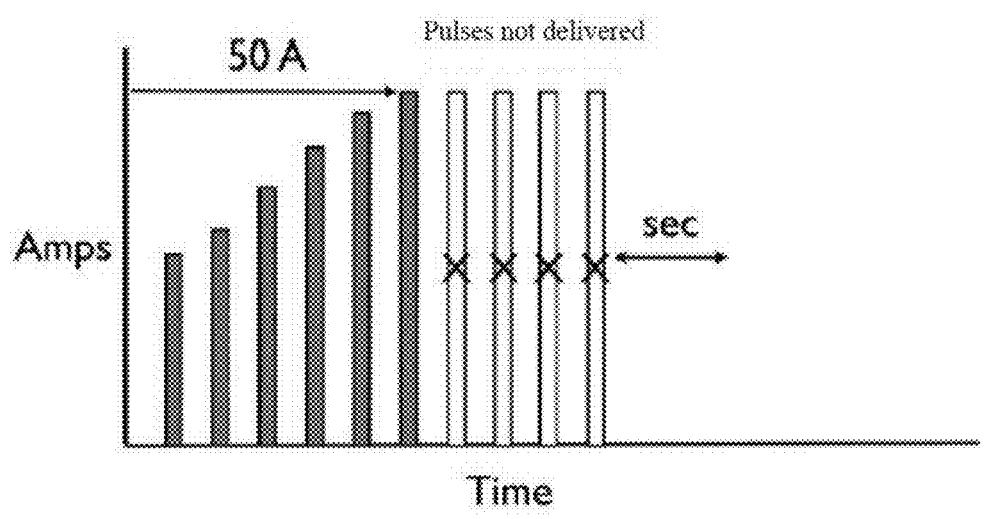
FIG. 6 is a diagram of a prior art failure to deliver prescribed pulses due to excess current.
Figure 7:
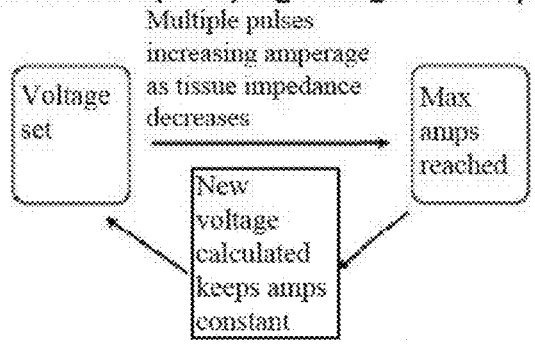
FIG. 7 is a schematic diagram of a feedback loop according to the present invention by which a controller reduces an applied signal voltage to keep the current amperage at or below a maximum.
Figure 8:
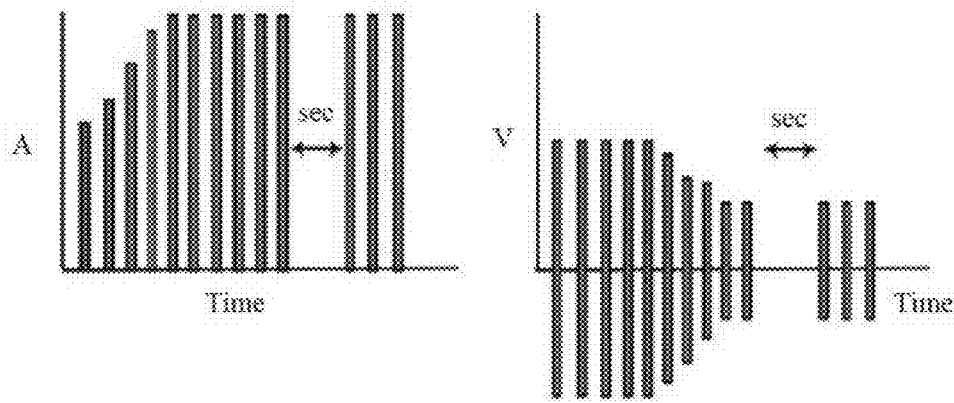
FIG. 8 is a diagram of a reduction in applied signal voltage upon reaching a maximum current level to permit continued signal delivery according to the present invention.

In yet another embodiment, the controller may monitor or determine current flow through the tissue during treatment for the purpose of avoiding overheating while yet permitting treatment to continue by reducing the applied voltage. Reduction in tissue impedance during treatment due to charge buildup and membrane rupture can cause increased current flow which engenders additional heating at the treatment site. With reference to FIG. 6, prior treatment methods have suffered from a need to cease treatment when the current exceeds a maximum allowable such that treatment goals are not met. As with direct temperature monitoring, the present invention can avoid the need to stop treatment by reducing the applied voltage and thus current through the tissue to control and prevent undesirable clinically significant thermal effects. Modulation of pulse duration and pulse burst interval duration may also be employed by the controller 11 for this purpose as described.

Figures 11, 12:
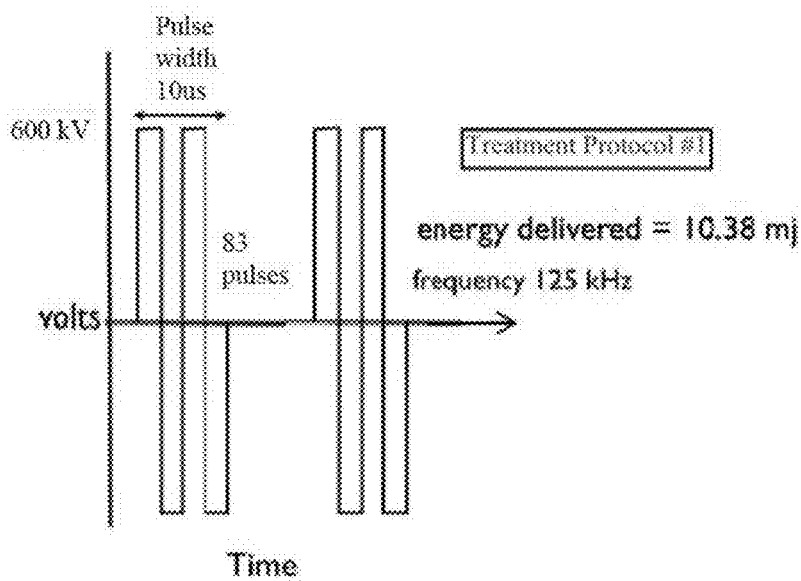
FIG. 11 is a chart of exemplary treatment protocol parameters according to the present invention.
FIG. 12 is a diagram of the parameters of exemplary treatment protocol number 1.

With reference to FIG. 11, four exemplary RF-EMB treatment protocols are detailed. With additional reference to FIG. 12, in protocol 1, a pulse train of 83 pulses 32 each a 10 ms duration is applied at 600 volts to electrodes spaced at 1 cm resulting in a field strength of 600 V/cm between the electrodes. In this example the applied pulses are bipolar with a frequency of 125 kHz with a pulse width of 10 ms, such that the total energy applied over the 0.83 seconds du-ration of the pulse train was 10.38 mJ. These treatment models and the total energy delivered were referenced from work describing energy parameters used for membrane breakdown of algae by, Foltz, G., Algae Lysis With Pulsed Electric Fields, California State Polytechnic University, San Luis Obispo 2012. Foltz demonstrated this energy requirement using unipolar pulses, without the advantage of instant charge reversal pulses, making this the worst case scenario for energy requirements to produce EMB.

Figure 13:
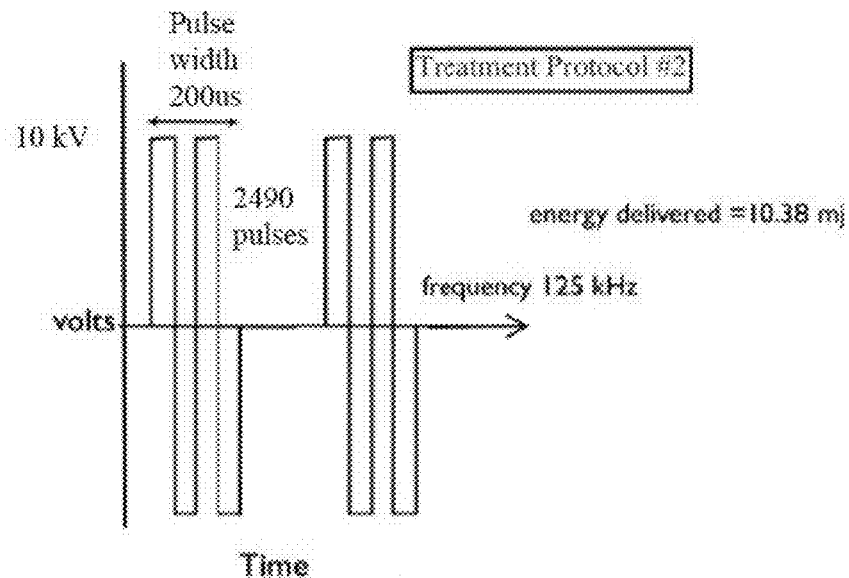
FIG. 13 is a diagram of the parameters of exemplary treatment protocol number 2.
Figure 14:
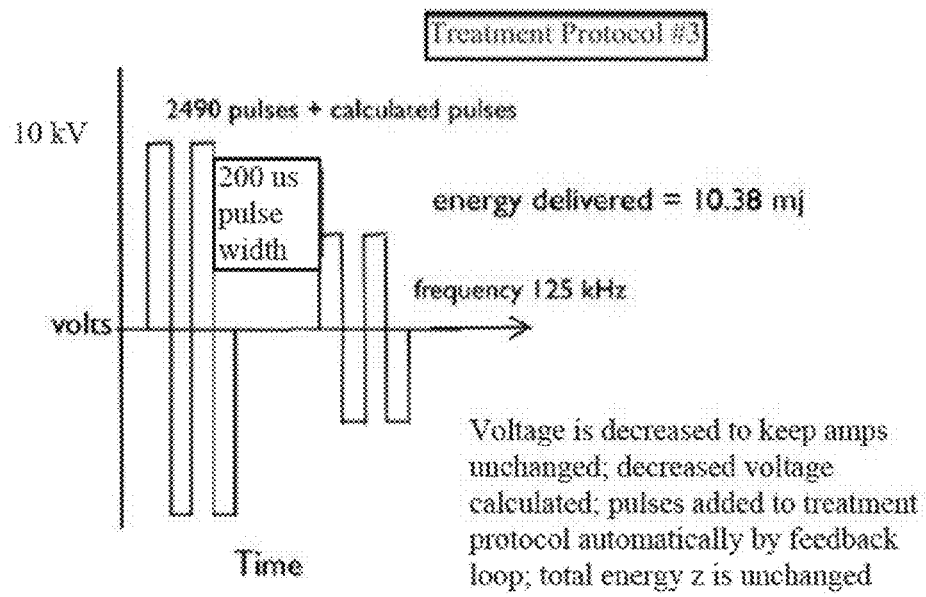
FIG. 14 is a diagram of the parameters of exemplary treatment protocol number 3.
Figure 15:
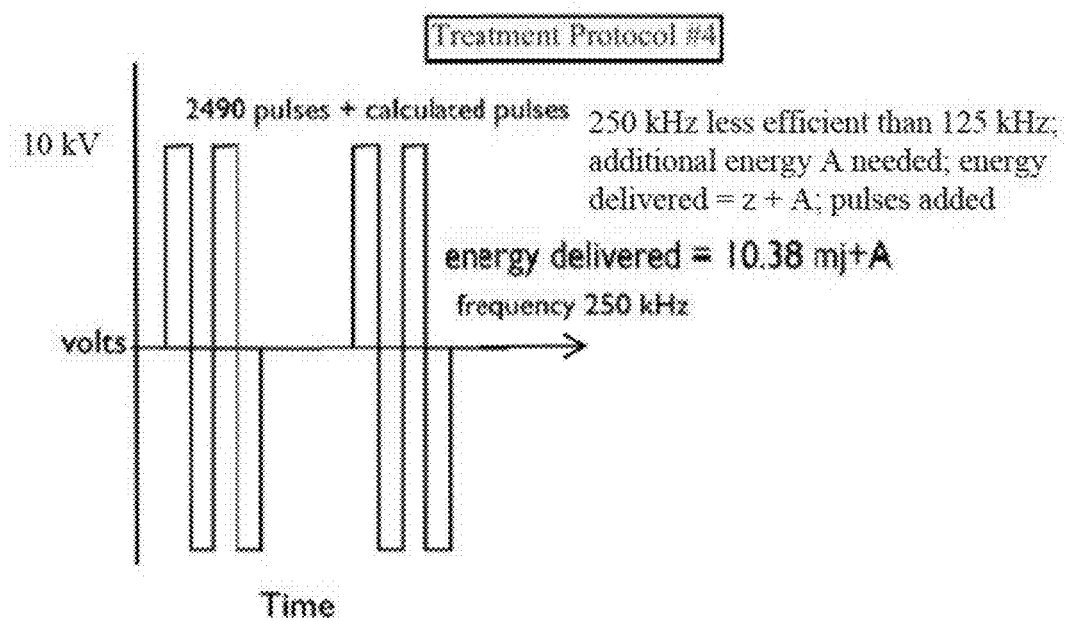
FIG. 15 is a diagram of the parameters of exemplary treatment protocol number 4.

With reference to FIG. 13, in protocol 2 EMB is achieved by a pulse width decreased to 200 µs and pulse train extended to 2490 pulses in a 10 kV/cm field for a total treatment time of 0.49 seconds. The total applied energy is again 10.38 mJ. With reference to FIG. 14, in protocol 3 additional pulses above the initially targeted 2490 are added by the controller 11 to compensate for reduction in voltage/field strength during treatment based on feedback from the treatment site. With reference to FIG. 15, in protocol 4 the additional pulses above the initially targeted 2490 are added to compensate for loss of efficiency resulting from the 250 kHz signal as compared to the 125 kHz signal frequency in the previous exemplary protocols.

The method of ablating undesirable soft tissue of the present invention is carried out by first identifying the location of the soft tissue within the subject to be ablated. Tissue identification may be done by known medical imaging techniques such as CT or MRI. The target soft tissue may or may not be a malignancy but rather need only be tissue that is undesirable in its present location for some reason. After identification of the target tissue, the preferred position and spacing of the electrodes relative to target soft tissue is determined based on the location and shape of the tissue to be ablated, the shape and location of adjacent structures, the dielectric constant and the conductivity of the target and surrounding soft tissue. Typically from 1 to 6 needle type probe electrodes are used. The electrodes are introduced into position in and around the treatment and connected to a controller for controlled delivery of the electric pulses for field generation and treatment. The probe electrodes may include a temperature sensor such as a thermocouple for reading and signaling to the controller the local temperature at or near the electrode. Placement and positioning of the electrodes may preferably be confirmed by medical imaging. The pulse generator is activated by the controller to apply electrical pulses to the electrodes to generate the treatment field as described above thereby causing electrical membrane breakdown of some or all of cells of said soft tissue.

Electrical membrane breakdown causes immediate spillage of all intracellular components of the ruptured cells into an extracellular space and exposes the internal constituent part of the cell membrane to the extracellular space. The intracellular components include cellular antigens and the internal constituent parts of the cell membrane include antigens specific to the cell membrane which induce an immunologic response to destroy and remove this and like material in the body of the subject. Like material may be other material in the body of the subject having the same cellular antigens or cell membrane specific antigens at locations remote from the treatment site including metastatic tissue. The immunologic response can be enhanced by administration of drugs that increase the immunologic response process including drugs which block inhibition of the CTLA-4 inhibitory signal of cytotoxic lymphocytes or that binds to S100A9 and modulating regulatory myeloid cell functions. Such drugs can be administered by any means, including without limitation, intravenously, orally or intramuscularly and may further be injected directly into or adjacent to the target soft tissue immediately before or after applying the EMB electric field. Such immunologic response enhancing drug may be comprised also of autologous dendritic cells.

Electrical membrane breakdown causes immediate, visually observable tissue change, cellular membrane destruction and cell death. As a result, the method may include the biopsy of a portion of the treated target tissue to verify treatment efficacy immediately after completion of the treatment while the patient is still in position for additional treatment. Additional treatment may be immediately administered based on the biopsy result and visual determination of treatment efficacy.

In yet another alternate embodiment of the present invention, with or without intermediate biopsy and visual observation for efficacy, the mode of treatment according to the present invention may be switched from EMB to thermal ablation without removal or repositioning of the electrodes. A switch to thermal ablation may be desirable to control bleeding at the tissue site or for direct destruction of undesirable tissue in concert with the RF-EMB. The switch may occur within a single pulse train by operation of the controller, or may be accomplished by a second or additional pulse train directed to RF thermal ablation only. The switch is accomplished by reconfiguring the signal generated by the pulse generator to increase the tissue temperature at the electrodes according to known RF thermal techniques.

Having now fully set forth the preferred embodiment and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

We claim:

1. A method of ablating undesirable soft tissue in a living subject, comprising the steps of:
   identifying a location of said soft tissue within said subject;
   determining a position, of at least one electrode relative to said soft tissue;
   introducing said at least one electrode to said position within said subject, said electrode electrically connected to a controller for controlling the delivery of electric pulses to said electrode, said controller comprising an electric pulse generator;
   applying to said soft tissue an electric field sufficient to cause electrical membrane breakdown of a cell membrane of a plurality of cells of said soft tissue to cause immediate spillage of all intracellular components into an extracellular space and exposure of an internal constituent part of said cell membrane to said extracellular space, said electric field applied to said soft tissue by delivering from said pulse generator to said at least one electrode at least one bi-polar pulse train configured to cause said electrical membrane breakdown, said bi-polar pulse train comprising at least two bi-polar electric pulses, each said bi-polar electric pulse in said bi-polar pulse train being separated by an inter pulse burst interval during which no voltage is applied to said at least one electrode;
   wherein a voltage of each of said bi-polar electric pulses is from 0.5 kV to 10 kV; and
   wherein a tissue change, cellular membrane destruction and cell death are visually observable in a sample of said undesirable soft tissue taken immediately after applying said electric field to said soft tissue; and farther comprising the steps of,
   after applying said electric field to said soft tissue by delivering said bi-polar pulse train, immediately biopsying a portion of said soft tissue to determine an efficacy of said ablation;
   if said efficacy exceeds a pre-determined threshold, ceasing said ablation of undesirable soft tissue; and
   if said efficacy does not exceed said pre-determined threshold, delivering from said pulse generator to said at least one electrode at least one additional bi-polar electric pulse so as to apply to said soft tissue a second electric field.

2. The method of claim 1 wherein a frequency of said electric field is from 14.2 kHz to less than 500 kHz.

3. The method of claim 2 wherein said frequency of said electric field is from 100 kHz to 450 kHz.

4. The method of claim 2 wherein said voltage over time of each of said bi-polar electric pulses traces a square waveform for a positive and negative component of a polarity oscillation.

5. The method of claim 2 wherein said voltage of each of said bi-polar electric pulses is characterized by waveforms with an instant charge reversal, between the positive and negative charge of each cycle.

6. The method of claim 1 wherein the duration of each of said at least one bi-polar electric pulses is from 100-1000 μs.

7. The method of claim 1, wherein said determining step further comprises the steps of estimating or measuring the dielectric constant and the conductivity of said soft tissue.

8. The method of claim 1, further comprising the step of configuring said bi-polar pulse train delivered to said at least one electrode from said pulse generator such that said electric field causes no clinically significant thermal damage to said soft tissue.

9. The method of claim 8, wherein said bi-polar pulse train is configured such that said field causes a temperature of said soft tissue to rise to not more than 50 degrees Celsius.

10. The method of claim 1, further comprising at least one additional bi-polar electric pulse to form a second bi-polar pulse train, wherein said second bi-polar pulse train is comprising a second series of not less than 100 bi-polar electric pulses configured so that said second electric field is sufficient to cause electrical membrane breakdown of said cell membrane of a plurality of cells of said soft tissue.

11. The method of claim 1, further comprising the step of introducing a temperature probe proximal to said at least one electrode, said probe operatively connected to said controller and reporting a temperature reading to said controller, said controller controlling varying at least one character of said at least one bi-polar electric pulse in response to said reported temperature.

12. The method of claim 11, wherein said temperature probe is a thermocouple.

13. The method of claim 11, wherein said temperature probe is integral to said at least one electrode and introduced therewith.

14. The method of claim 11, wherein said bi-polar pulse train comprises a series of not less than 100 bi-polar electric pulses, each of said bi-polar electric pulses in said bi-polar pulse train being separated by an inter pulse burst interval during which no voltage is applied to said at least one electrode; and further comprising the steps of storing in a memory of said controller at least one temperature set-point; and
   altering by said controller for at least a portion of said series at least one of a pulse duration, said inter pulse burst interval and a total number of bi-polar electric pulses in said bi-polar pulse train in response to said temperature reading reported to said controller from said probe exceeding said set point.

15. The method of claim 14, further comprising the step of initiating said altering step in response to said temperature reported by said probe falling below said set-point.

16. The method of claim 14, wherein said altering step comprises reducing said pulse duration.

17. The method of claim 15, wherein said altering step comprises increasing said inter pulse burst interval.

18. The method of claim 16, wherein said altering step comprises reducing the number of bi-polar electric pulses in said bi-polar pulse train.

19. The method of claim 1, further comprising the steps of
   storing in a memory of a controller at least one maximum current set-point, said controller controlling said delivery of said at least two bi-polar electric pulses;
   determining by said controller a current through said at least one electrode; and
   reducing said voltage of said at least two bi-polar electric pulses delivered to said at least one electrode when said current equals said maximum current set-point whereby said current is prevented from exceeding said set point.

20. The method of claim 1 wherein said intracellular components comprises a cellular antigen and said internal constituent part of said cell membrane further comprises an antigen specific to, said cell membrane; and further comprising the step of administering to said subject an immunologic response enhancing drug to increase said immunologic process of said subject which is activated to remove said, intracellular components and internal constituent part of said cell membrane from said extracellular space.

21. The method of claim 20 wherein said immunologic response enhancing drug blocks inhibition of the CTLA-4 inhibitory signal of cytotoxic lymphocytes.

22. The method of claim 20 wherein said immunologic response enhancing drug is administered by one of intravenously, orally or intramuscularly.

23. The method of claim 20 wherein said immunologic response enhancing drug is injected directly into or adjacent to undesirable soft tissue before or after said step of applying to said soft tissue an electric field.

24. The method of claim 20 wherein said immunologic response enhancing drug is comprised of autologous dendritic cells.

25. The method of claim 20 wherein said immunologic response enhancing drug binds to S100A9 and modulating regulatory myeloid cell functions.

26. The method of claim 20 wherein said immunologic response enhancing drug is comprised of autologous dendritic cells.

27. The method of claim 1, wherein said bi-polar pulse train is a series of not less than 100 bi-polar electric pulses.

28. A method of ablating undesirable soft tissue in a living subject, comprising the steps of:

identifying a location of said soft tissue within said subject;

determining based on a tissue type of said soft tissue a minimum energy profile necessary to be applied to a cell of said soft tissue to cause cell membrane rupture by electrical membrane breakdown;

determining a position of at least one electrode relative to said cell mass;

introducing said at least one electrode to said position within said subject, said electrode electrically connected to a controller for controlling the delivery of electric pulses to said electrode, said controller comprising an electric pulse generator;

determining based on said minimum energy profile and said position of said at least one electrode an electric field strength necessary to apply to said cell mass said minimum energy profile;

determining based on said electric field strength a bi-polar electric pulse train profile having not less than 100 pulses, said pulse train profile characterized by a pulse number, pulse duration and inter pulse burst intervals, said pulses each having a frequency and a voltage, said voltage characterized by an instantaneous reversal of polarity;

delivering from said pulse generator to said at least one electrode by said controller a series of electric pulses according to said electric pulse train profile whereby a pulsed electric field is generated, said field applying sufficient energy to a plurality of said cells of said soft tissue to cause cell death by electrical membrane breakdown.

* * * * *